(12) United States Patent
Maassarani

(10) Patent No.: US 10,420,628 B2
(45) Date of Patent: Sep. 24, 2019

(54) DENTAL COVERING REMOVAL TOOL

(71) Applicant: Sami Maassarani, Birmingham, MI (US)

(72) Inventor: Sami Maassarani, Birmingham, MI (US)

(*) Notice: Subject to any disclaimer, the term of this patent is extended or adjusted under 35 U.S.C. 154(b) by 0 days.

(21) Appl. No.: 15/595,211

(22) Filed: May 15, 2017

(65) Prior Publication Data

US 2017/0354479 A1 Dec. 14, 2017

Related U.S. Application Data

(63) Continuation of application No. 15/186,991, filed on Jun. 20, 2016, now Pat. No. 9,687,316.
(60) Provisional application No. 62/348,374, filed on Jun. 10, 2016.

(51) Int. Cl.
| | |
|---|---|
| *A61C 3/16* | (2006.01) |
| *A61C 7/02* | (2006.01) |
| *A61D 5/00* | (2006.01) |
| *A61B 17/00* | (2006.01) |

(52) U.S. Cl.
CPC ............ *A61C 3/162* (2013.01); *A61C 7/023* (2013.01); *A61D 5/00* (2013.01); *A61B 2017/0023* (2013.01); *A61C 3/16* (2013.01); *A61C 2203/00* (2013.01)

(58) Field of Classification Search
CPC ....... A61C 3/162; A61C 3/16; A61C 2203/00; A61C 7/023; A61B 2017/0023; A61D 5/00
See application file for complete search history.

(56) References Cited

U.S. PATENT DOCUMENTS

| | | |
|---|---|---|
| 659,182 A | 10/1900 | Pilling |
| 840,580 A | 1/1907 | McMillan |
| 936,695 A | 10/1909 | Barth |
| 1,130,281 A | 3/1915 | Hay |
| 1,472,462 A | 10/1923 | De Port |
| 2,057,077 A | 10/1936 | Zimmer |
| 2,602,998 A | 7/1952 | Sprague |
| 2,723,661 A | 11/1955 | Hull |

(Continued)

FOREIGN PATENT DOCUMENTS

| | | |
|---|---|---|
| CA | 2720442 A1 | 5/2012 |
| CN | 201320222 Y | 12/2008 |

*Primary Examiner* — Cris L. Rodriguez
*Assistant Examiner* — Hao D Mai
(74) *Attorney, Agent, or Firm* — The Dobrusin Law Firm, P.C.; Daniela M. Thompson-Walters

(57) ABSTRACT

A device for removing a dental covering having: (a) an engagement portion, having a first plate portion which is substantially flat, that is configured to contact a portion of the dental covering along only one of a facial side or a lingual side of the dental covering; (b) a load applying portion, connected to the engagement portion and having a second plate portion which is substantially flat, which is adapted to rest upon an adjacent surface relative to the dental covering; and (c) an intermediate portion which is integral with and adjacent to both the engagement portion and the load applying portion; and wherein the first plate portion is parallel to the second plate portion. The device may be a dental covering removal tool which may find particular use in removing dental coverings, such as temporary and permanent crowns.

18 Claims, 7 Drawing Sheets

(56) References Cited

U.S. PATENT DOCUMENTS

| | | | |
|---|---|---|---|
| 3,898,738 A | 8/1975 | Linder | |
| 3,911,583 A | 10/1975 | Hoffman | |
| 3,986,265 A * | 10/1976 | Cusato | A61C 7/04 433/4 |
| 4,197,647 A | 4/1980 | Goldenthal | |
| 4,204,330 A | 5/1980 | Ford | |
| 4,230,454 A * | 10/1980 | Lococo | A61C 3/14 433/153 |
| 4,594,069 A * | 6/1986 | Thompson | A61C 3/16 433/157 |
| 4,904,183 A | 2/1990 | Hannan | |
| D308,804 S | 6/1990 | Hisscott | |
| 5,015,185 A * | 5/1991 | Cane | A61C 3/16 433/153 |
| 5,057,016 A | 10/1991 | Lukase et al. | |
| 5,122,058 A | 6/1992 | Lukase et al. | |
| 5,421,721 A | 6/1995 | Fyffe | |
| D359,894 S | 7/1995 | Pomeroy | |
| 5,538,421 A * | 7/1996 | Aspel | A61C 7/04 433/159 |
| 5,820,368 A | 10/1998 | Wolk | |
| 5,833,460 A | 11/1998 | Maeda | |
| 5,928,254 A | 7/1999 | Jensen | |
| 6,352,291 B1 | 3/2002 | Tortajada | |
| 6,382,965 B1 * | 5/2002 | Ruiz-Vela | A61C 7/02 433/4 |
| 6,394,805 B1 | 5/2002 | Rabal | |
| 6,413,088 B1 | 7/2002 | Kawaguchi | |
| D463,554 S | 9/2002 | Li | |
| 6,575,749 B1 | 6/2003 | Greenwald | |
| 6,752,380 B1 | 6/2004 | Taylor | |
| D506,118 S | 6/2005 | Rau | |
| 6,910,890 B2 | 6/2005 | Golden | |
| 7,011,517 B2 | 3/2006 | Nicozisis | |
| D627,886 S | 11/2010 | Williamson | |
| 8,062,030 B2 | 11/2011 | Saubers | |
| 8,152,525 B2 | 4/2012 | Rossi | |
| D666,668 S | 9/2012 | Present | |
| 8,376,741 B2 | 2/2013 | Bednaz | |
| 8,435,033 B2 | 2/2013 | Gross | |
| 8,475,166 B1 | 7/2013 | LaMee | |
| D734,852 S | 7/2015 | Lim | |
| 9,084,650 B2 | 7/2015 | McCarthy | |
| 2003/0091958 A1 | 5/2003 | Muller | |
| 2003/0152887 A1 | 8/2003 | Freeman | |
| 2005/0064358 A1 * | 3/2005 | Nicozisis | A61C 7/02 433/3 |
| 2005/0272006 A1 | 12/2005 | Rosenberg | |
| 2006/0131906 A1 | 6/2006 | Maurer | |
| 2007/0020581 A1 * | 1/2007 | Whitehead | A61C 3/162 433/144 |
| 2007/0026357 A1 | 2/2007 | Farber | |
| 2007/0072142 A1 | 3/2007 | Staines | |
| 2007/0122763 A1 * | 5/2007 | Farzin-Nia | A61C 7/02 433/4 |
| 2010/0047740 A1 | 2/2010 | Fyffe | |
| 2011/0045435 A1 | 2/2011 | Goodman | |
| 2013/0078592 A1 | 3/2013 | McCarthy | |
| 2013/0230817 A1 | 9/2013 | Kabbani | |
| 2013/0244201 A1 | 9/2013 | Lim | |
| 2013/0288196 A1 | 10/2013 | Gordon | |
| 2014/0315148 A1 * | 10/2014 | Chang | A61C 3/162 433/159 |
| 2015/0335396 A1 | 11/2015 | Block | |

* cited by examiner

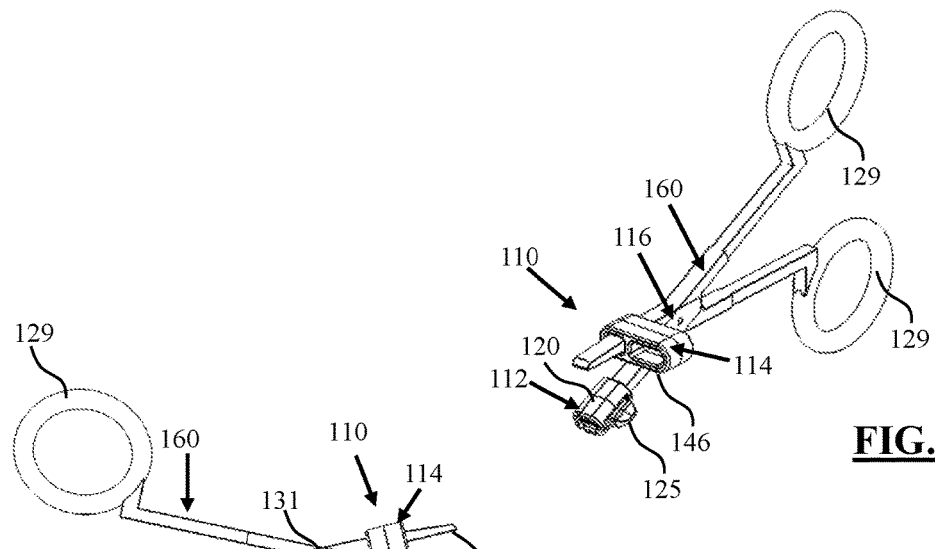
FIG.-12
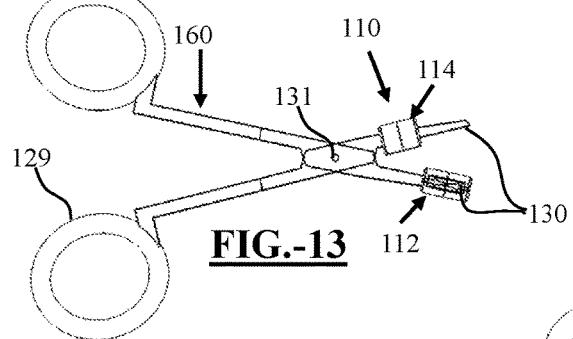
FIG.-13
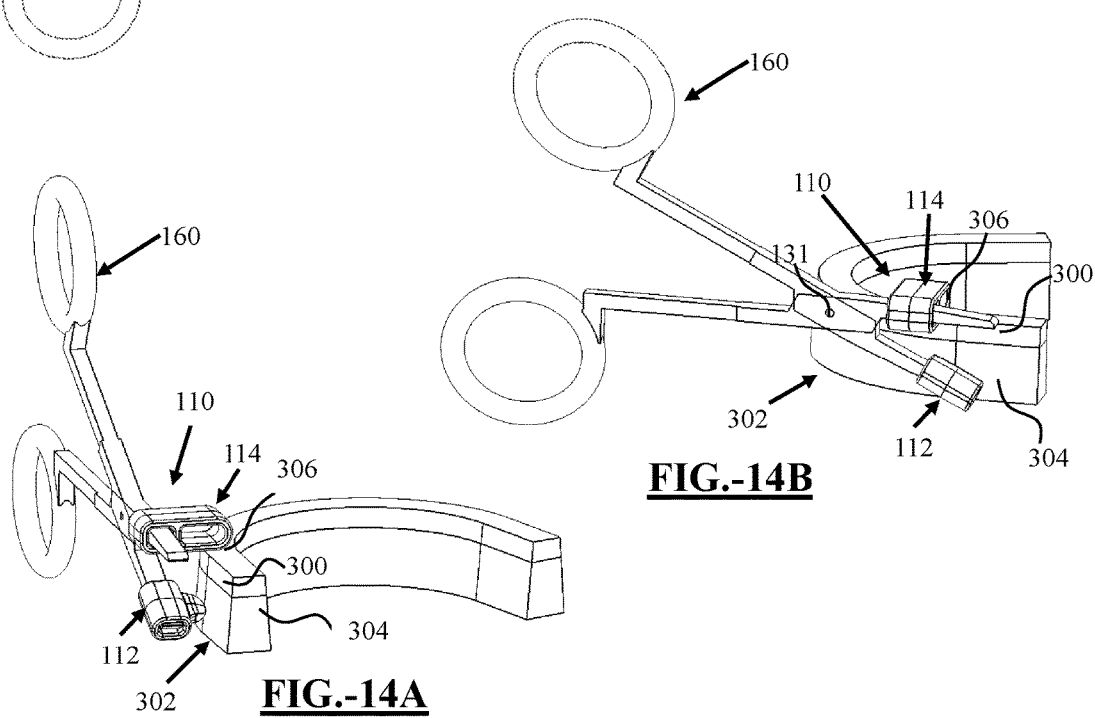
FIG.-14A
FIG.-14B

DENTAL COVERING REMOVAL TOOL

FIELD

The present disclosure relates to a dental covering removal tool, which may be useful for removing a dental covering from an underlying structure. The present disclosure may specifically relate to a dental covering removal tool which is adapted to assist a dental operator in removing temporary and permanent crowns from a patient's mouth.

BACKGROUND

In dental practice, while a permanent crown is fabricated for a patient, a patient is fitted with a temporary covering (e.g. such as a temporary crown). The temporary covering protects the original underlying tooth or post and allows a patient to maintain normal chewing while waiting for the permanent crown to be fabricated. The temporary covering is typically adhered with a short term dental adhesive to the underlying tooth or post. To ensure the temporary covering does not cause patient discomfort, the temporary covering may need to be removed multiple times during fitting. To expose the underlying tooth or post once the permanent crown is fabricated, the temporary covering needs to be removed from the patient's mouth.

Generally, for removal of a temporary dental covering, many dental operators (i.e., dental physicians) pinch grip the temporary dental covering to remove the covering from the underlying tooth or post. Hand and finger access may be limited. For example, the further toward the rear of a mouth of a patient, the more restricted the space for a dental physician's hand to access the dental covering. While removing the dental covering, a dental operator's hand may block visual access to the dental covering. To overcome access space, provide better control, and provide better visual access, hemostats, forceps and dental pliers have been utilized. Forceps style dental tools present the challenges of needing to contact opposing surfaces of a dental covering (i.e., lingual side and facial side) to apply a grip force. The grip force provided by these tools may result in damage to the dental covering, such as cracking and breaking. The size of these forceps style dental tools may result in patient discomfort. Generally, these forceps style tools are meant for long-term use due to their initial purchase cost.

US 2013/0244201; US 2011/0045435; U.S. Pat. Nos. 6,394,805; and 6,413,088 disclose varying forceps dental tools for removing dental coverings. U.S. Pat. No. 9,084,650 discloses a dental removal apparatus for removing dental appliances with a pry force. Notwithstanding the above, there appears to be an absence of a simple prying tool which can pry a dental covering (e.g. one located within a mouth of a patient) from an underlying surface without damaging the dental covering or the underlying surface.

What is needed is a tool which is relatively small yet easy to insert into a mouth of a patient. What is needed is a tool which is simple to manipulate within a mouth of a patient. What is needed is a tool which can pry a dental covering from an underlying surface. What is needed is a tool which does not damage a dental covering, adjacent teeth, and/or adjacent tissue. What is needed is a tool, at least a part of, which is disposable after a single use. What is needed is a tool which is cost effective to manufacture, store, ship, and/or purchase.

SUMMARY

The present disclosure provides for a device and a method for removing a dental covering. The device may be a simple tool which is relatively small, easy to insert into a mouth of a patient, and easy to manipulate once inserted into a mouth of the patient. The device may include at least two planar and/or plate-like portions. The device may be configured so that an operator is able to manipulate the device with two fingers to pry a dental covering from an underlying surface. The device may be adapted for ambidextrous use by an operator. The device may be configured for removing a dental covering in any or all of the four quadrants of a mouth of a patient. At least a portion of the device may be disposable to allow for single use. A portion of the device may be adapted for resting within a surface in a mouth of a patient. A portion of the device may be adapted for pivoting within a mouth of a patient to pry a dental covering off from an underlying surface. A portion of the device may include a portion which is adapted for contacting and prying the dental covering off from an underlying surface. The device may include a projection, wedge, cut-out, tapered thickness, or any combination thereof to easily locate the device in direct contact with the dental covering, apply the pry force, or both.

The present disclosure relates to a device for removing a dental covering comprising: (a) an engagement portion that is configured to contact a portion of the dental covering along only one of a facial side or a lingual side of the dental covering and receive a prying load applied by an operator; and (b) a load applying portion connected to the engagement portion which is adapted to rest upon an adjacent surface relative to the dental covering and be pivoted upwardly or downwardly by application of the prying load.

In some preferred embodiments, the device may include an intermediate portion. The intermediate portion may be configured to bridge the engagement portion and load applying portion to impart a torque force on the engagement portion from the load applying portion. The intermediate portion may be configured to transfer the prying load from the load applying portion to the engagement portion. The intermediate portion may be configured to provide clearance so the intermediate portion substantially avoids contact with any teeth or tissue adjoining the dental covering. In some preferred embodiments, the device may have a longitudinal axis and/or a longitudinal plane which may generally extend from the engagement portion to the load applying portion. In some preferred embodiments, the device may be sufficiently symmetrical about the longitudinal axis and/or the longitudinal plane to allow for ambidextrous use of the device. In some preferred embodiments, the dental covering may be for a human or animal tooth. In some preferred embodiments, the dental covering may include a temporary crown, a permanent crown, a dental bridge, a dental brace, a dental veneer, an artificial tooth, the like, or any combination thereof. In some preferred embodiments, the adjacent surface may be a tooth adjacent the dental covering. In some preferred embodiments, the device may be a unitary structure. In some preferred embodiments, the device may include a handle. In some preferred embodiments, the device may comprise biodegradable plastic.

The present disclosure further relates to a method of using the device of the disclosure to remove a dental covering from a mouth of a patient comprising: (i) contacting an engagement portion to the portion of the dental covering; (ii) resting a load applying portion upon an adjacent surface relative to the dental covering; and (iii) applying a prying load by a hand of an operator and removing the dental covering from the mouth of the patient.

The present disclosure may provide a device for removing a dental covering. The present disclosure may provide a device which is easy to insert and simple to manipulate in a patient's mouth. The present disclosure provides a device which can pry a dental covering from an underlying surface. The present disclosure provides a device which is able to pry a dental covering without compression forces about opposing surfaces of the exterior of the dental covering. By eliminating compression forces about the dental covering, the device is able to reduce damage to the dental covering or adjacent teeth. The device may be biodegradable, which may allow the device to be at least partially disposable after a single use. The device may be a unitary plastic structure which may provide for a device which is easy to manufacture and low in cost.

BRIEF DESCRIPTION OF DRAWINGS

FIG. 12 illustrates a perspective view of a device according to the teachings applied to a hemostat.

FIG. 13 illustrates a side view of a hemostat including the device according to the teachings.

FIG. 14A illustrates a perspective view of a device according to the teachings removing a dental covering from a mouth of a patient.

FIG. 14B illustrates a side view of a device according to the teachings removing a dental covering from a mouth of a patient.

DETAILED DESCRIPTION

Figure 1:
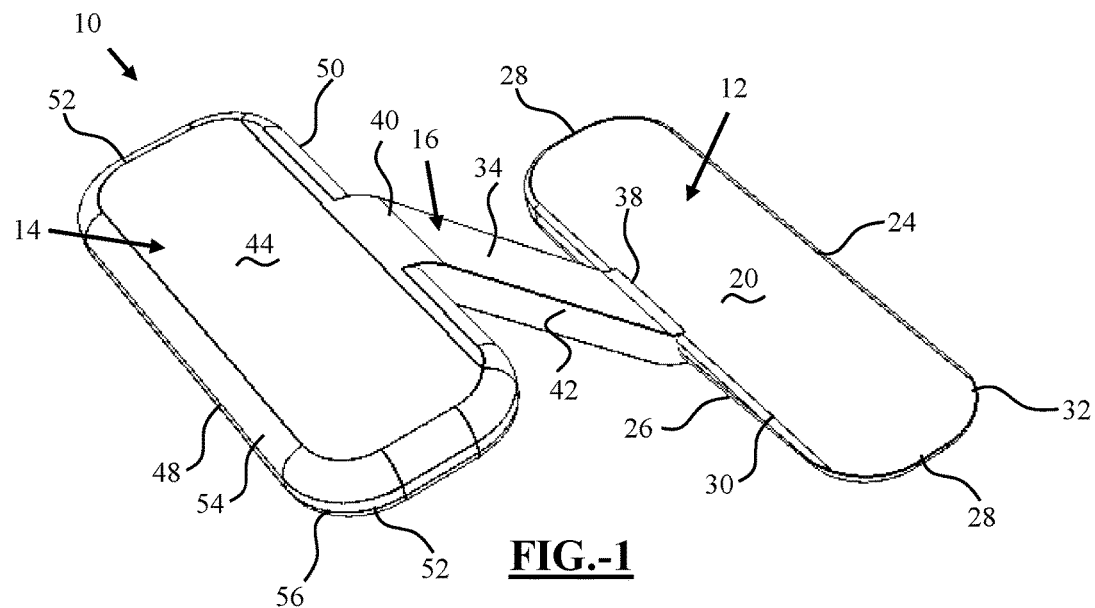
FIG. 1 is a perspective view of a device according to the teachings.

The explanations and illustrations presented herein are intended to acquaint others skilled in the art with the present teachings, its principles, and its practical application. The specific embodiments of the present teachings as set forth are not intended as being exhaustive or limiting of the present teachings. The scope of the present teachings should be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present disclosure provides for a device and a method for removing a dental covering. The device may be a simple tool which is relatively small, easy to insert into a mouth of a patient, and easy to manipulate once inserted into a mouth of the patient. At least a portion of the device may be disposable to allow for single use. The device may include a portion (e.g., a load applying portion, a handle, or both) to easily control and manipulate the device by an operator. The device may include a portion (i.e., load applying portion) which may rest within a surface in a mouth of a patient. The device may include a portion (e.g. an engagement portion) to contact and pry the dental covering off from an underlying surface. A portion (e.g., such as the engagement portion) may include a projection, wedge, cut-out, tapered thickness, or any combination thereof to easily locate the device in direct contact with the dental covering, apply the pry force, or both. The device may include one or more portions (i.e., load applying portion and/or intermediate portion) and/or surfaces which function as a fulcrum. The device may allow an operator to hold the device, applying a prying load, and pivot about the fulcrum. By pivoting about the fulcrum, the prying load may transfer to a portion (i.e., engagement portion) to pry the dental covering from the underlying surface.

The device of the disclosure may find particular use for removal of a dental covering. A dental covering may include any type of dental restoration, inlay, overlay, or the like. A dental covering may include a temporary crown, a permanent crown, a dental bridge, a dental brace, a dental veneer, an artificial tooth, or any combination thereof. A dental covering may be affixed or adhered to an underlying tooth or post with a temporary or short term dental adhesive. A dental covering may be for a human or animal tooth. The device of the disclosure may be configured to contact a portion of the dental covering for removal. A portion of the dental covering may include an extremity of the dental covering. An extremity of the dental covering may include an exterior side surface, an exterior surface adjacent a patient's gum line, or both. The portion of the dental covering may be part of the facial side, lingual side, or both. The device of the disclosure may be configured to rest on an adjacent surface to the dental covering to remove the dental covering. An adjacent surface may include any surface adjacent the dental covering. An adjacent surface may include an adjacent tooth. An adjacent tooth may include a tooth, a dental covering, a dental prosthetic, the like, or any combination thereof.

The disclosure relates to a device for removing a dental covering. The device may be a unitary structure or a multi-piece structure. The device includes an engagement portion and a load applying portion. The engagement portion may be configured to contact a portion of the dental covering along only one of a facial side or a lingual side of the dental covering and receive a prying load applied by an operator. The load applying portion may be connected to the engagement portion. The load applying portion may be adapted to rest upon an adjacent surface relative to the dental covering. The load applying portion may be adapted to be pivoted upwardly or downwardly by application of a prying load.

The device may include an intermediate portion. The intermediate portion may connect the load applying portion and the engagement portion. The intermediate portion may be configured to bridge the engagement portion and the load applying portion to impart a torque force on the engagement portion from the load applying portion. The intermediate portion may provide clearance so the intermediate portion substantially avoids contact with any teeth or tissue adjoining the dental covering.

The device has an overall size. The overall size may allow the device to be sufficiently small to allow a plurality of devices to be stored within a dental office while utilizing minimal space. The overall size may allow the device to be efficiently packaged for shipping and/or storage. The overall size may allow the device to be inserted into a mouth of a patient while helping to prevent patient discomfort due to the size of the device. The overall size of the device may include a length, width, and height of the device. The length of the device may be a distance along a longitudinal axis, from a rear end to a front end, or both. The rear end may be a rear end of the load applying portion, a rear end of a handle, or both. A front end may be a front end of an engagement portion, a front end of a handle, a front end of a tip, or any combination thereof. The length of the device may be about 15 mm or greater, about 20 mm or greater, about 50 mm or greater, or even about 75 mm or greater. The length of the device may be about 200 mm or less, about 175 mm or less, about 150 mm or less, or even about 125 mm or less. The width of the device may be a distance generally perpendicular to a longitudinal axis, from one lateral end to another lateral end, or both. The width of the device may be about 9 mm or greater, about 13 mm or greater, or even about 20 mm or greater. The width of the device may be about 40 mm or less, about 35 mm or less, or even about 30 mm or less. The height of the device may be the distance from an upper surface to a lower surface, an engagement portion to a load applying surface, one end of a handle to another end of a handle, or any combination thereof. The height of the device may be about 10 mm or more, about 15 mm or more, or even about 20 mm or more. The height of the device may be about 75 mm or less, about 50 mm or less, or even about 30 mm or less.

The device includes a longitudinal axis. The longitudinal axis may generally extend from at least a portion of the load applying portion to at least a portion of the engagement portion. The device may include a longitudinal plane. The longitudinal plane may pass through the longitudinal axis. The longitudinal plane may be generally perpendicular to an upper surface of the engagement portion, an upper surface of the load applying portion, or both.

The device may be substantially symmetrical about the longitudinal axis, the longitudinal plane, or both. The device may be sufficiently symmetrical about the longitudinal axis, the longitudinal plane, or both to allow for ambidextrous use of the device. Ambidextrous use may include the device being adapted for use (i.e., application of a prying load) by a user's left hand or right hand. Ambidextrous use may include the device is adapted for removing a dental covering in an upper jaw, lower jaw, right side of a jaw, and/or left side of a jaw. Ambidextrous use may include the device is adapted for removing a dental covering in any of the four quadrants of a patient's mouth. Ambidextrous use may include contacting only one of a facial side or a lingual side of a dental covering with the engagement portion.

The device may include a transverse plane. The transverse plane may be generally parallel to the longitudinal axis, generally perpendicular to the longitudinal plane, or both. Generally parallel and generally perpendicular may include slight differences in degrees due to manufacturing tolerances (i.e., up to +/−15 degrees). The transverse plane may be generally parallel to at least a portion of the load applying portion, the engagement portion, or both. The transverse plane may be generally parallel to an upper surface of the load applying portion, the engagement portion, or both. The transverse plane may intersect a midpoint of the device. The midpoint may be located along the length of the intermediate portion. The engagement portion may be on an opposing side of the transverse plane as the load applying portion. The intermediate portion may be transverse to the transverse plane.

The device includes an engagement portion. The engagement portion may function to receive a prying load, apply a prying load, remove a dental covering, or any combination thereof. The engagement portion may be configured to contact a portion of a dental covering. The engagement portion may remove the dental covering by being wedged in between the dental covering and a patient's gum line. After being wedged, the engagement portion may apply or transfer a prying load to the dental covering. While applying or transferring the prying load to the dental covering, the engagement portion may lift or separate the dental covering from the underlying surface. The engagement portion may have any size or shape suitable for contacting a dental covering, removing a dental covering, receiving a prying load, applying a prying load, or any combination thereof. The engagement portion may be rectangular, square, oblong, elliptical, polygonal, the like, or any combination thereof. The engagement portion may be integral with or separate from a handle. The engagement portion may have an upper surface and a lower surface.

The engagement portion includes an upper surface. At least a portion of the upper surface may function to come into direct contact with the dental covering, apply the prying load to the dental covering, pry the dental covering from an adhering surface or any combination thereof. The upper surface may include a generally plate like surface (i.e., first flat plate portion). The upper surface, plate like surface, or both may be generally parallel to and distanced from an upper surface of the load applying portion, a plate like surface of the load applying portion, or both. The upper surface may be substantially uniform (i.e. smooth). The upper surface may include contouring (i.e., bowing, curving, cut-outs, notches) to engage with the dental covering. The upper surface opposes the lower surface of the engagement portion.

The engagement portion includes a lower surface. The lower surface may be generally parallel, at an angle, or both to the upper surface. A portion of the lower surface may be generally parallel to the upper surface. For example, a midsection of the lower surface may be generally parallel to a midsection of the upper surface. A portion of the lower surface may be opposing and at an angle to the upper surface. For example, at one or more lateral ends, the engagement portion may taper to a smaller thickness. At a smaller thickness, the lower surface may be at an angle to the upper surface. A tapered thickness may allow one or more lateral ends to wedge between a dental covering and a gumline. The lower surface may be curved with a radius. The lower surface may curve toward one or both of the lateral ends. The radius and/or curve of the lower surface may provide a rocking surface when a prying load is applied to the device. The rocking surface may assist in providing user comfort when the dental covering is pried from an underlying surface.

The engagement portion may have a thickness. The thickness may be the distance between the upper surface and the lower surface. The thickness may be substantially uniform, may taper towards one or more outside edges of the engagement portion, or may expand towards one or more outside edges of the engagement portion. The thickness may be from about 0.05 mm or greater, about 2 mm or greater, or even about 6 mm or greater. The thickness may be from about 12 mm or less, about 10 mm or less, or even about 8 mm or less. The engagement portion may have a length and a width. The length of the engagement portion may be the distance measured from edge to edge, generally parallel to a longitudinal axis of the device, distance from a front end to a rear end, a distance from an end opposing an end integrated with an intermediate portion, or any combination thereof. The length of the engagement portion may be about 5 mm or greater, 7 mm or greater, or even 9 mm or greater. The length of the engagement portion may be about 20 mm or less, about 18 mm or less, or even 14 mm or less. The width of the engagement portion may be the distance measured from a lateral edge to an opposing lateral edge, generally perpendicular to the longitudinal axis of the device or both. The width of the engagement portion may be greater than, equal to, or less than a width of the intermediate portion, load applying portion, or both. The width of the engagement portion may or may not include one or more extensions extending from the engagement portion. The width of the engagement portion may be about 9 mm or greater, about 13 mm or greater, or even about 20 mm or greater. The width of the engagement portion may be about 40 mm or less, about 35 mm or less, or even about 30 mm or less.

The engagement portion may be connected to an intermediate portion, a load applying portion, a handle, or any combination thereof. The engagement portion may include one or more receptacles. A receptacle of the engagement portion may cooperate or mate with a handle. The engagement portion may be generally parallel to a load applying portion. For example, an upper surface of the engagement portion may be generally parallel to an upper surface of a load applying portion.

The engagement portion may include an off-set extension. The off-set extension may function to come into direct contact with the dental covering, apply the prying load to the dental covering, pry the dental covering from an adhering surface, or any combination thereof. The off-set extension may be integral with the engagement portion, a handle, or both. The off-set extension may extend or protrude from a lateral side of the engagement portion. The off-set extension may have a thickness. The thickness may be measured as a distance between an upper and lower surface of the off-set extension. The off-set extension may be tapered. A tapered thickness may allow the off-set extension to wedge between a dental covering and a gumline. The thickness may be about 0.2 mm or greater, about 0.4 mm or greater, or even about 0.5 mm or greater. The thickness may be about 5 mm or less, about 3 mm or less, or even about 2 mm or less. The off-set extension may have a width. The width may be the distance between a lateral end of the engagement portion to a lateral end of the off-set extension. The width of the off-set extension may be about 2 mm or greater, about 4 mm or greater, or even about 5 mm or greater. The width of the off-set extension may be about 10 mm or less, about 8 mm or less, or even about 6 mm or less.

The device includes a load applying portion. The load applying portion may function to receive a prying load, transfer a prying load, provide a grip surface, retain a handle portion, connect to an engagement portion, or any combination thereof. The load applying portion may be configured to rest upon an adjacent surface relative to the dental covering. The load applying portion may be configured to be held by a user. The load applying portion may be configured to engage and retain a handle. The load applying portion may be configured to be pivoted upwardly or downwardly by application of the prying load. The load applying portion may receive a prying load from a user. The load applying portion may transfer the prying load to the intermediate portion, the engagement portion, or both. The load applying portion may have any size or shape suitable resting upon an adjacent surface, receiving a prying load, transferring a prying load, or any combination thereof. The load applying portion may be rectangular, square, oblong, elliptical, polygonal, the like, or any combination thereof. The load applying portion may be substantially symmetrical about a longitudinal axis or longitudinal plane of the device or may be asymmetrical. The load applying portion may be integral or separate from a handle. The load applying portion may have an upper surface and a lower surface.

The load applying portion includes an upper surface. At least a portion of the upper surface may function to receive a prying load from a user, provide a grip surface, provide a load application surface, or any combination thereof. The upper surface may include a generally plate like surface (i.e., second flat plate portion). The upper surface, plate like surface, or both may be generally parallel to and distanced from an upper surface of the engagement portion, a plate like surface of the engagement portion, or both. The upper surface may be substantially uniform (i.e. smooth) or non-uniform. The upper surface may include contouring (i.e., bowing, curving, cut-outs, notches) to providing a resting surface for a finger of a user. The upper surface opposes the lower surface of the load applying portion.

The load applying portion includes a lower surface. The lower surface may be generally parallel, at an angle, or both to the upper surface. At least a portion of the lower surface may be generally parallel to the upper surface. For example, a mid-section of the lower surface may be generally parallel to a midsection of the upper surface. A portion of the lower surface may be opposing and at an angle to the upper surface. For example, towards one or more edges, the load applying portion may expand to a larger thickness. At a larger thickness, the lower surface may be at an angle to the upper surface. A larger thickness of the load applying portion may function to provide a larger grip or pinch surface for a user, house a receptacle, or both.

The load applying portion may have a thickness. The thickness may be the distance between the upper surface and the lower surface. The thickness may be substantially uniform, may taper towards one or more outside edges of the load applying portion, or may increase towards one or more outside edges of the load applying portion. The thickness may be from about 0.05 mm or greater, about 2 mm or greater, or even about 6 mm or greater. The thickness may be from about 12 mm or less, about 10 mm or less, or even about 8 mm or less. The load applying portion may have a length and a width. The length of the load applying portion may be the distance measured from edge to edge, generally parallel to a longitudinal axis of the device, the distance between a front end and a rear end of the load applying portion, the distance between an end connected to or integrated with an intermediate portion and an opposing end, or any combination thereof. The length of the load applying portion may be about 5 mm or greater, 7 mm or greater, or even 9 mm or greater. The length of the load applying portion may be about 20 mm or less, about 18 mm or less, or even 14 mm or less. The width of the load applying portion may be the distance measured from a lateral edge to an opposing lateral edge, generally perpendicular to the longitudinal axis of the device or both. The width of the load applying portion may be greater than, equal to, or less than a width of the intermediate portion, engagement portion, or both. The width of the load applying portion may be about 9 mm or greater, about 13 mm or greater, or even about 20 mm or greater. The width of the load applying portion may be about 40 mm or less, about 35 mm or less, or even about 30 mm or less. The load applying portion may be connected to an intermediate portion, an engagement portion, a handle, or any combination thereof.

The load applying portion may include one or more receptacles. A receptacle of the load applying portion may cooperate or mate with a handle. The load applying portion may include one or more grip features for aiding a user to grip the load applying portion. The one or more grip features may include dimples, indentations, non-slip material, the like, or any combination thereof. The load applying portion may be generally parallel to the engagement portion. For example, an upper surface of the load applying portion may be generally parallel to an upper surface of an engagement portion.

The device may include an intermediate portion. The intermediate portion may function to receive a prying load, transfer a prying load, connect an engagement portion with a load applying portion, provide clearance for the device to remove a dental covering, or any combination thereof. The load applying portion may be configured to bridge the engagement portion and the load applying portion. The load applying portion may be adapted to impart a torque force on the engagement portion from the load applying portion. The load applying portion may transfer a prying load from the load applying portion to the engagement portion. The intermediate portion may provide a clearance. The clearance may allow the intermediate portion to substantially avoid contact with any teeth or tissue adjoining the dental covering. The clearance may allow at least a portion of the engagement portion to contact a dental covering, wedge between the dental covering and a gumline, or both. The intermediate portion may be integral with or separate from the load applying portion, engagement portion, or both. The intermediate portion may be rectangular, square, oblong, elliptical, polygonal, the like, or any combination thereof. The intermediate portion may be substantially symmetrical about a longitudinal axis or longitudinal plane of the device or may be asymmetrical.

The intermediate portion may have an upper surface and a lower surface. The upper surface of the intermediate portion may be integral or extend from at least a portion of the upper surface of the engagement portion, the load applying portion, or both. The lower surface of the intermediate portion may be integral or extend from at least a portion of lower surface of the engagement portion, the load applying portion, or both.

The intermediate portion may have a thickness. The thickness may be the distance between the upper surface and the lower surface of the intermediate portion. The thickness may be substantially uniform, may be non-uniform, may taper towards one or more outside edges of the intermediate portion, may increase towards one or more outside edges of the intermediate portion, may be larger at or near areas with reinforcement structures, or any combination thereof. The thickness may at least include portions with a thickness greater than, equal to, or less than the thickness of the load applying portion, the engagement portion, or both. The thickness may be from about 0.05 mm or greater, about 2 mm or greater, or even about 6 mm or greater. The thickness may be from about 12 mm or less, about 10 mm or less, or even about 8 mm or less. The load applying portion may have a length and a width. The length of the load applying portion may be the distance measured from an end adjacent to or integral with the engagement portion to an end adjacent to or integral with the load applying portion. The length of the load applying portion may be about 5 mm or greater, 8 mm or greater, or even 10 mm or greater. The length of the load applying portion may be about 20 mm or less, about 18 mm or less, or even 15 mm or less. A midpoint of the device may be located along the length of the intermediate portion. The midpoint may be halfway along the length of the intermediate portion or may be off-set.

The width of the intermediate portion may be the distance measured from a lateral side to an opposing lateral side. The width of the intermediate portion may be greater than, equal to, or less than a width of the load applying portion, engagement portion, or both. Preferably, the width of the intermediate portion is substantially less (i.e., thinner) than both the load applying portion and the engagement portion. The difference in the widths between the intermediate portion from the load applying portion and the intermediate portion from the engagement portion may provide clearance for the intermediate portion. The width of the intermediate portion may be about 2 mm or greater, about 3 mm or greater, or even about 5 mm or greater. The width of the intermediate portion may be about 30 mm or less, about 25 mm or less, or even about 20 mm or less.

The intermediate portion may reside generally in a plane. The intermediate portion and/or the plane may be transverse to at least a portion of the engagement portion, load applying portion, or both. The intermediate portion may be transverse to a first plate portion of the engagement portion, a first plate portion of the load applying portion, or both. The load applying portion and/or the engagement portion may project away from the intermediate portion, the plane of the intermediate portion, or both. The intermediate portion may be transverse with at least a portion of the engagement portion, the load applying portion, or both so as to form alternate exterior angles. An alternate exterior angle may be formed by the lower surface of the load applying portion and the lower surface of the intermediate portion. An alternate exterior angle may be formed by the upper surface of the engagement portion and the upper surface of the intermediate portion, or both. The alternate exterior angles may be obtuse. The alternate exterior angles may be about 90 degrees or greater, about 110 degrees or greater, or even about 120 degrees or greater. The alternate exterior angles may be about 150 degrees or less, about 140 degrees or less, or even about 135 degrees or less.

The device may include one or more reinforcement structures. The reinforcement structures may function to reinforce the device when receiving and/or transferring a prying load, increasing the load bearing capability of the device, increasing strength of the device, or any combination thereof. The one or more reinforcement structures may allow the device to be sufficiently rigid to withstand the prying load. The reinforcement structures may allow the device to be sufficiently rigid to transmit at least a portion of the prying load to the engagement portion. The one or more reinforcement structures may be part of the intermediate portion. The one or more reinforcement structures may run along all or a portion of the length of the intermediate portion. The one or more reinforcement structures may be located at an upper surface, a lower surface, or both of the intermediate portion. The one or more reinforcement structures may extend at least partially into the engagement portion, the load applying portion, or both. The one or more reinforcement structures may include one or more rib structures, a stiffer material, localized thickness, the like, or any combination thereof.

The device may include one or more receptacles. The one or more receptacles may function to engage a handle, engage a load applying portion, engage one or more tips of a handle, or any combination thereof. The one or more receptacles may be located in the engagement portion, the load applying portion, a handle or any combination thereof. The one or more receptacles may have any size or shape suitable for engaging a handle, one or more tips of a handle, a load applying portion, or any combination thereof. The one or more receptacles may engage at least a portion of a handle (i.e., a connection portion, one or more tips) and/or a portion of the load applying portion (i.e., a threaded protrusion, a tab extension, etc) with a press fit, friction fit, lock fit, threaded fit, snap fit, cantilever snap fit, annular snap fit, a channel fit, the like, or any combination thereof. The one or more receptacles, connection portion, one or more tips, or any combination thereof may include an anti-rotation feature. For example, the anti-rotation feature may include one or more slots extending from the receptacle. The one or more receptacles may have a threaded bore. The threaded bore may engage with a threaded portion of a handle or the load applying portion. A threaded bore may provide for a threaded fastener fit with a portion of a handle. The one or more receptacles may have a geometry similar and/or reciprocal to a portion of a handle or a load applying portion. For example, the one or more receptacles may have a polygonal shape reciprocal to a polygonal shape of a portion of a handle or load applying portion. The similar and/or reciprocal geometry may provide for a friction fit or lock fit with a portion of a handle. The one or more receptacles may include a channel in the handle or the load applying portion. The channel may be a C-Channel, track channel, or similar. The channel may adapted to receive and engage a slide or track mating portion of the load applying portion or handle.

One or more receptacles may be sized differently than one or more other receptacles. A first receptacle may have a larger height and width than a second receptacle. A first receptacle may be located in the engagement portion. A second receptacle may be located in the load applying portion. The second receptacle may be larger than the first receptacle. A larger second receptacle may allow the load applying portion to be off-set from the engagement portion. By off-setting the engagement portion from the load applying portion, the engagement portion is configured to contact a portion of a dental covering and the load applying portion is configured to rest upon an adjacent surface. For example, the second receptacle may have a friction fit further down a length of a handle as opposed to the first receptacle. The second receptacle may allow the load applying portion to engage with a tip of a handle close to a joint of a handle (i.e., pivot joint of a hemostat, pliers, or forceps).

The device may include a handle. The handle may function to receive a prying load, transfer a prying load, provide a grip surface, or any combination thereof. The handle may have any size or shape suitable for receiving a prying load, transferring a prying load, providing at least one grip surface, or any combination thereof. The handle may include only a single grip surface. For example, the handle may be generally rod shaped, solid, include a single grip surface, or any combination thereof. The handle may include one portion, two portions, a pivot joint, more than one grip surface, or any combination thereof. For example, the handle may be a hemostat, dental pliers, dental forceps, or the like. A pivot joint may allow a distance between an engagement portion and load applying portion to be adjusted. By adjusting the distance, the pivot joint may allow the device to be adjusted for varying heights of dental coverings. The handle may be integral with any portion of the device or may be a separate.

A handle may be integral with or separate from the load applying portion, the engagement portion, or both. The handle may extend from the load applying portion, the engagement portion, or both. The handle may extend in a generally opposing direction from the load applying portion as the engagement portion. By extending away from the engagement portion, the handle may extend the device outside of a patient's mouth. By extending the device outside of a patient's mouth, the handle may facilitate manipulation of the device. The handle may include at least one grip. The grip may make the handle more ergonomic for use by a user's hand (i.e., larger grip surface, cushion).

A handle may include at least one connecting portion. The connecting portion may be at an opposite end of the handle as the grip. The connecting portion may function to mate the handle with any portion of the device. The connecting portion may mate the handle with the load applying portion. The connecting portion may have an exterior geometry to engage and be retained within a receptacle of the load applying portion. For example, the connecting portion may be threaded, include a tab, have similar and reciprocal geometry to the shape of a receptacle, include a channel or channel track, or the like.

A handle may include one or more tips. For example, a first tip and a second tip of a hemostat, pliers, forceps, or the like. The first tip and the second tip may be received within one or more receptacles. For example, the first tip may be received within a first receptacle (i.e., receptacle in the load applying portion). For example, the second tip may be received within a second receptacle (i.e., receptacle in the engagement portion).

The device may include one or more features for preventing discomfort, damage and/or injury in a mouth of a patient. The intermediate portion, the engagement portion, the load applying portion, or any combination thereof may include beveled or rounded edges. The rounded edges may help prevent the device from cutting or uncomfortably pressing share edges into tissue of a patient's mouth.

The device may be comprised of any material suitable for receiving the prying load, transferring the prying load, removing a dental device, preventing permanent deformation of the device, preventing damage to the dental covering and/or other teeth, being at least partially disposable, being reusable, or any combination thereof. The device may be comprised of a material which avoids substantial permanent deformation after use of the device to apply a prying load. The device may be comprised of plastic, rubber, metal, the like, or any combination thereof. The device may be biodegradable. The device may be comprised of biodegradable plastic. For example, the load applying portion, the intermediate portion, the engagement portion, the handle, or any combination thereof may comprise biodegradable plastic. One or more portions of the device may be comprised of different material than one or more other portions of the device. For example, a handle may comprise a different material as the load applying portion, the intermediate portion, and/or the engagement portion. For example, a handle may comprise metal or non-biodegradable plastic.

The disclosure further relates to a method of using the device of the disclosure to remove a dental covering from a mouth of a patient. The method includes contacting the engagement portion to the portion of the dental covering; resting the load applying portion upon the adjacent surface relative to the dental covering; and applying the prying load by a hand of the operator and removing the dental covering from the mouth of the patient.

The method may include engaging a handle with the load applying portion, the engagement portion, or both. Engaging the handle may include locating or inserting a portion (i.e., a connection portion, one or more tips) of a handle into the load applying portion, the engagement portion, or both. The handle may be inserted into one or more receptacles. Engaging the handle may include securing the handle via a threaded fit, snap fit, friction fit, channel fit, or any combination thereof. The method may include inserting or receiving a connection portion in the load applying portion. The method may include inserting a first tip of a handle into the engagement portion. The method may include inserting a second tip of a handle into a load applying portion. The method may include removing a handle from the load applying portion, the engagement portion, or both. The method may include sterilizing any portion of the device prior to contact the engagement portion to a dental covering.

The method includes contacting the engagement portion to a portion of the dental covering. A portion of the dental covering may be an extremity of the dental covering. Contacting the dental covering may include placing a lateral edge of the engagement portion adjacent to and in direct contact with a portion of the dental covering. Contacting the dental covering may include placing the upper surface of the engagement portion in direct contact with a base of a dental covering. Contacting the dental covering may include placing an off-set extension in direct contact with a portion of the dental covering. Contacting the dental covering may include wedging the engagement portion between a patient's gum line and the base of the dental covering.

The method includes resting the load applying portion upon an adjacent surface relative to the dental covering. Resting the load applying portion may include locating the lower surface of the load applying portion onto an adjacent surface.

The method includes applying a prying load by a hand of the operator. Applying the prying load may include applying the prying load simultaneously to an engagement portion and a load applying portion. Applying a prying load may include gripping a handle. Applying a prying load may include applying a load to the handle. The load may be applied to an end of a handle.

The prying load may be a combination of at least two loads. The prying load may include at least one linear force. The prying load may include at least one rotational force (i.e., torque). The at least two loads may be applied at one location or at least at two locations. The prying load may include an engagement load, a lifting load, or both. An engagement load may include a linear force. A lifting load may include a torque. The prying load may be applied to a single handle by a hand of a user. The handle may transfer the prying load to a load applying portion. The load applying portion may function as a fulcrum. The load applying portion may transfer the prying load to the intermediate portion, the engagement portion, or both. The prying load may be applied by at least two fingers of a hand of a user. A first finger may be in direct contact with the engagement portion. The first finger may be in direct contact with the lower surface of the engagement portion. The first finger may apply at least a rotational force. The rotational force may result in the dental covering moving away from the gumline. A second finger may in in direct contact with the load applying portion. The second finger may be in direct contact with an upper surface of the load applying portion. The second finger may apply at least a linear force. The linear force may be in a direction toward the adjacent surface. The linear force may retain the load applying portion in direct contact with the adjacent surface. The linear force may allow the load applying portion, the junction between the load applying portion and an intermediate portion, or both to act as a fulcrum. By applying the rotational force and the linear force simultaneously, the engagement portion may rotate at least partially about the fulcrum. By rotating partially about the fulcrum, the engagement portion removes the dental covering.

The method includes removing the dental covering from the mouth of a patient. Removal of the dental covering may include lifting a dental covering from an underlying tooth, post, or other adhesive surface. Removal of the dental covering may include at least partially rotating the engagement portion about a fulcrum. Removal of the dental covering may include overcoming an adhesion force. The adhesion force may be provided a temporary dental glue or cement.

The disclosure further relates to a kit comprising the device of the disclosure. The kit may include packaging. The kit may include a dental adhesive. Dental adhesive may include dental glue, dental cement, or the like. The kit may include a cleaning device. The cleaning device may remove dental adhesive. For example, the cleaning device may remove dental adhesive from an underlying tooth or post after removal of the dental covering. The kit may include a handle. The handle may be adapted to engage with the device. The kit may include a single handle or a plurality of handles. The kit may include a single device or a plurality of devices. For example, the kit may include a single handle with a plurality of disposable devices. The single handle may be for repetitive use. The disposable devices may be one-time use devices.

Illustrative Embodiments

The following descriptions of the Figures are provided to illustrate the teachings herein, but are not intended to limit the scope thereof. Features of one embodiment may be employed in another embodiment. For example, any combination of the features of FIGS. 8-11 may be incorporated into any of the device as shown in of FIGS. 1-5 and 12-18. For example, any combination of the features of FIGS. 1-5 may be incorporated into FIGS. 12-18 and vice-versa.

FIG. 1 is a perspective view of a device 10 for removing a dental covering 300 (not shown). The device 10 is a unitary structure. The device 10 includes an engagement portion 12 and a load applying portion 14. The engagement portion 12 includes an upper surface 20 opposing a lower surface 22 (not shown). The upper surface 20 is shaped like a generally flat plate or is a flat plate portion. The engagement portion 12 has an overall generally rectangular shape. The engagement portion 12 includes four side surfaces. The side surfaces include a rear end 26, front end 24, and two lateral ends 28. The rear end 26 is adjacent to and connected with an intermediate portion 16. The front end 24 is distanced from and opposing the rear end 26. The rear end 26 and front end 24 are connected and adjacent to two lateral ends 28. The engagement portion 12 includes beveled edges 30 about at least some of the side surfaces. The engagement portion 12 includes rounded corners 32. The engagement portion 12 is connected to the load applying portion 14 by an intermediate portion 16. The intermediate portion 16 extends from the rear end 26 of the engagement portion 12.

FIG. 1 further illustrates the intermediate portion 16 includes an upper surface 34 opposing a lower surface 36 (not shown). The upper surface 34 is shaped like a generally flat plate or is a flat plate portion. The intermediate portion 16 has an overall generally rectangular shape. The intermediate portion 16 includes two opposing lateral ends 42. The lateral ends 42 are generally parallel in a plane to the lateral ends 28 of the engagement portion 12. The lateral ends 42 are adjacent and connected to the front end 38 and rear end 40 of the intermediate portion 16. The front end 38 of the intermediate portion 16 is integrated with the rear end 26 of the engagement portion. The rear end 40 of the intermediate portion 16 is integrated with a front end 50 of the load applying portion 14. The intermediate portion 16 distances the load applying portion 14 from the engagement portion 12 so that the load applying portion 14 and engagement portion 12 are generally parallel and distanced from one another.

FIG. 1 shows the load applying portion 14 includes an upper surface 44 opposing a lower surface 46 (not shown). The upper surface 44 is shaped like a generally flat plate or is a flat plate portion. The load applying portion 14 has an overall generally rectangular shape. The load applying portion 14 includes four side surfaces. The side surfaces include a rear end 48, front end 50, and two lateral ends 52. The front end 50 is adjacent to and connected with an intermediate portion 16. The front end 50 is distanced from and opposing the rear end 48. The rear end 48 and front end 50 are connected and adjacent to two lateral ends 52. The load applying portion 14 includes beveled edges 54 about the side surfaces. The load applying portion 14 includes rounded corners 56.

Figure 2:
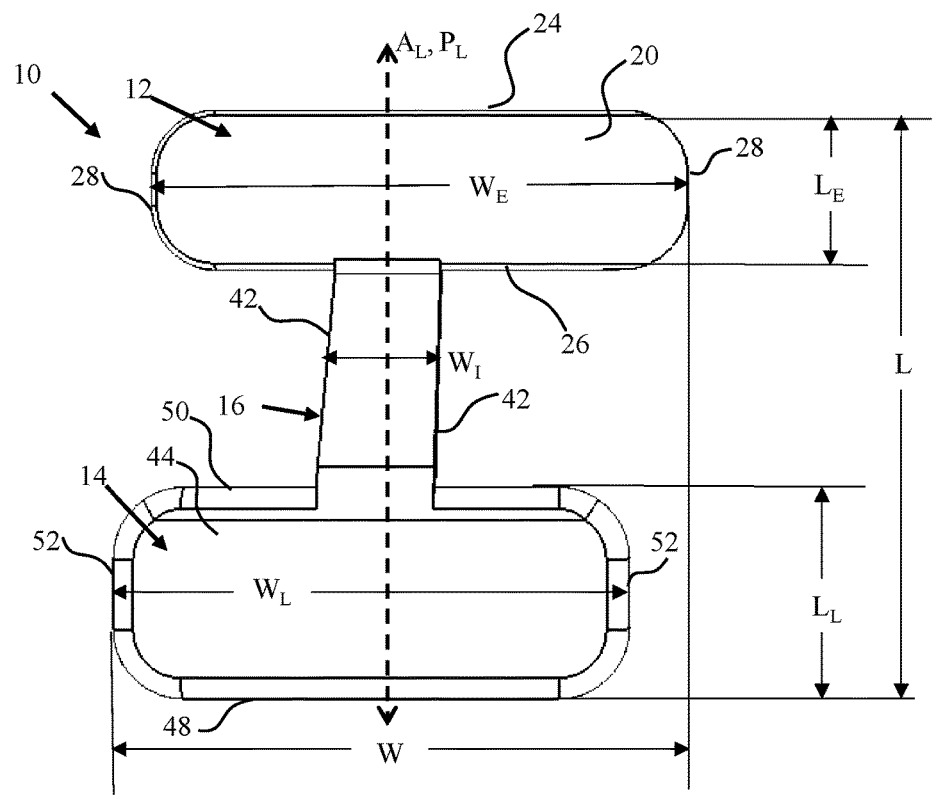
FIG. 2 illustrates a top view of a device according to the teachings.

FIG. 2 is a top view of a device 10 for removing a dental covering 300 (not shown). The device 10 includes a longitudinal axis $A_L$ which generally extends from the engagement portion 12 to the load applying portion 14. A longitudinal plane $P_L$ intersects through the longitudinal axis $A_L$. The device 10 may be sufficiently symmetrical about the longitudinal axis $A_L$ and/or the longitudinal plane $P_L$ to allow for ambidextrous use of the device 10. The device has an overall length L which is the distance between the front end 24 of the engagement portion 12 to the rear end 48 of the load applying portion 14. The device has an overall width W which is the widest width of the device 10. In FIG. 2, the width W is the distance from the most outwardly lateral end 52 of the load applying portion 14 to the most outwardly lateral end 28 of the engagement portion 12.

FIG. 2 illustrates the engagement portion 12 includes a width $W_E$ which is the distance between the two lateral ends 28. The intermediate portion 16 includes a width $W_I$ which is the distance between the two lateral ends 42. The width $W_I$ of the intermediate portion 16 is smaller than the width $W_E$ of the engagement portion 12. The load applying portion 14 includes a width $W_L$ which is the distance between the two lateral ends 52 of the load applying portion 14. The width $W_I$ of the intermediate portion 16 is smaller than the width of $W_L$ of the load applying portion 14.

FIG. 2 further illustrates the engagement portion 12 and load applying portion 14 each have a length $L_E$, $L_L$. The length $L_E$ of the engagement portion 12 is the distance between the front end 24 and the rear end 26 of the engagement portion. The length $L_L$ of the load applying portion 14 is the distance between the front end 50 and rear end 48 of the load applying portion 14.

Figure 3:
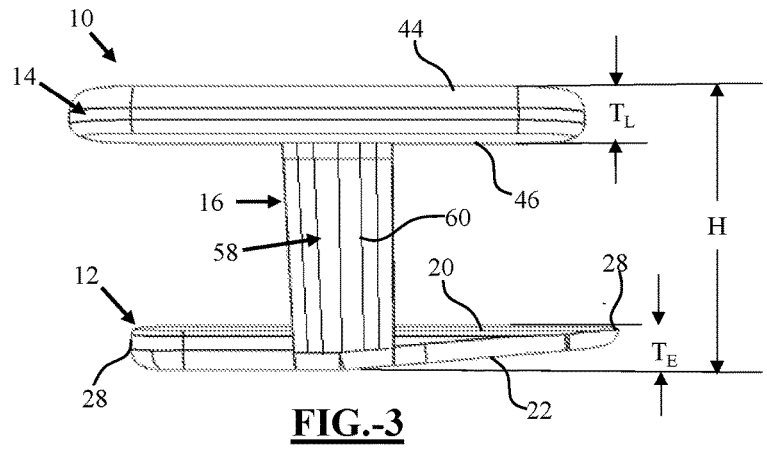
FIG. 3 illustrates a rear view of a device according to the teachings.

FIG. 3 illustrates a rear view of the device 10. The device 10 has an overall height H. The height H is the distance from an upper surface 44 of the load applying portion 14 to a lower surface 22 of the engagement portion 12. The load applying portion 14 is distanced from the engagement portion 12 by an intermediate portion 16. The load applying portion 14 has a thickness $T_L$. The thickness $T_L$ is the distance between the upper surface 44 and the lower surface 46. The thickness $T_L$ of the load applying portion 14 is generally consistent across the entire width $W_L$ (not shown) of the load applying portion 14. The engagement portion 12 has a thickness $T_E$. The thickness $T_E$ is the distance between the upper surface 20 and the lower surface 22. The thickness $T_E$ of the engagement portion 12 is generally consistent along a midsection of the width $W_E$ of the engagement portion 12. The thickness $T_E$ tapers towards one of the lateral ends 28 of the engagement portion 12. The thickness $T_E$ may taper towards both of the lateral ends 28 of the engagement portion.

FIG. 3 further illustrates one or more reinforcement structures 58. The intermediate portion 16 includes one or more reinforcement structures 58. The one or more reinforcement structures include one or more ribs 60. One or more ribs 60 extend at least partially into the engagement portion 12, the load applying portion 14, or both.

Figure 4:
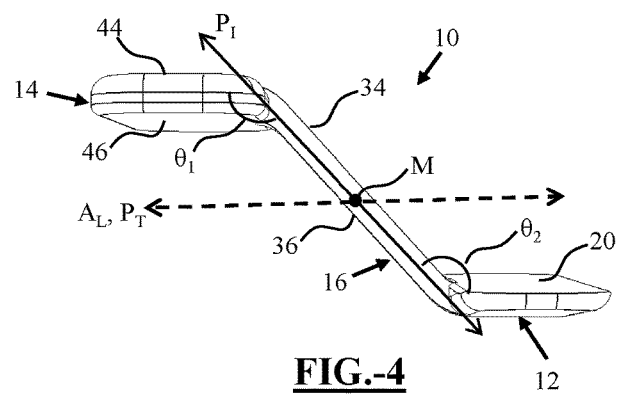
FIG. 4 illustrates a side view of a device according to the teachings.

FIG. 4 illustrates a side view of the device 10. The device includes a longitudinal axis $A_L$ which generally extends from the engagement portion 12 to the load applying portion 14. The intermediate portion 16 includes a midpoint M. The midpoint M is located between the engagement portion 12 and the load applying portion 14. The midpoint M intersects the longitudinal axis $A_L$. A transverse plane $P_T$ runs generally parallel to the engagement portion 12, the load applying portion 14, or both. The transverse plane $P_T$ runs generally parallel to the longitudinal axis $A_L$ and is generally perpendicular to the longitudinal plane $P_L$ (not shown). The longitudinal axis $A_L$ may lie in the transverse plane $P_T$. The transverse plane $P_T$ intersects the midpoint M. The engagement portion 12 is located on one side of the transverse plane $P_T$. The load applying portion 14 is located on an opposing side of the transverse plane $P_T$ as the engagement portion 12.

FIG. 4 further illustrates the intermediate portion 16 lies in generally a single plane $P_I$. The single plane $P_I$ is transverse to the engagement portion 12 (i.e., plate portion 20) and the load applying portion 14 (i.e. plate portion 44). The upper surface 20 of the engagement portion 12 and the upper surface 44 of the load applying portion 14 each project away from the single plane $P_I$. The upper surfaces 20, 44 project away from the single plane $P_I$ in opposing directions. The upper surfaces 20, 44 project away from the single plane $P_I$ to form alternate exterior angles $\Theta_1$, $\Theta_2$. One alternate exterior angle $\Theta_1$ is formed by the lower surface 36 of the intermediate portion 16 and the lower surface 46 of the load applying portion 14. Another alternate exterior angle $\Theta_2$ is formed by the upper surface 34 of the intermediate portion 16 and the upper surface 20 of the engagement portion 12. The alternate exterior angles $\Theta_1$, $\Theta_2$ are obtuse.

Figure 5:
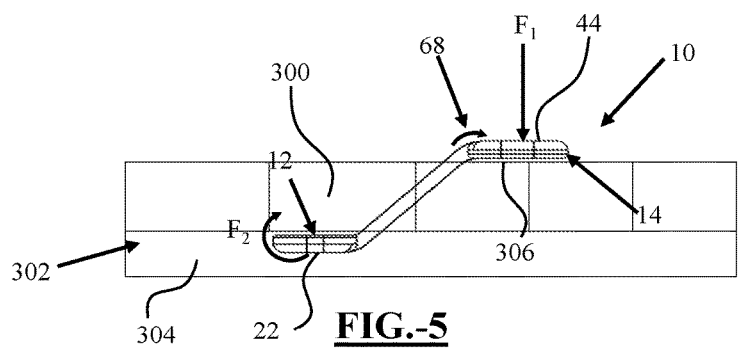
FIG. 5 illustrates a side view of a device according to the teachings removing a dental covering from a mouth of a patient.

FIG. 5 illustrates a side view of the device 10 removing a dental covering 300 from a patient's mouth 302. The load applying portion 14 rests on an adjacent surface 306 to the dental covering 300. The engagement portion 12 contacts a portion of the dental covering 300. The engagement portion 12 contacts a portion of the dental covering 300 adjacent the gumline 304. To lift the dental covering 300, a linear force $F_1$ is applied to the load applying portion 14. The linear force $F_1$ is directed toward the upper surface 44 of the load applying portion 14 and toward the adjacent surface 306. To lift the dental covering 300, a rotational force $F_2$ is applied to the engagement portion 12. The rotational force $F_2$ is applied to the lower surface 22 of the engagement portion 12. The application of the linear force $F_1$ and the rotational force $F_2$ results in a fulcrum 68. The device 10 may pivot about the fulcrum 68 to pry the dental covering 300 from an underlying surface (not shown). The fulcrum 68 may be located between or on a portion of the load applying portion 14, the intermediate portion 16, or both.

Figure 7:
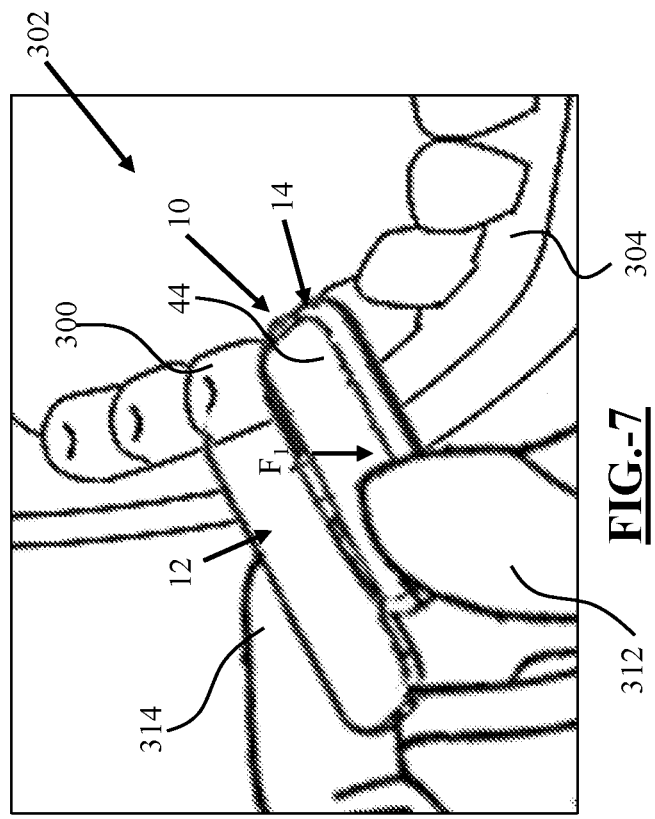
FIG. 7 illustrates a close-up view of a device according to the teachings in a mouth of a patient to remove a dental covering.
Figure 6:
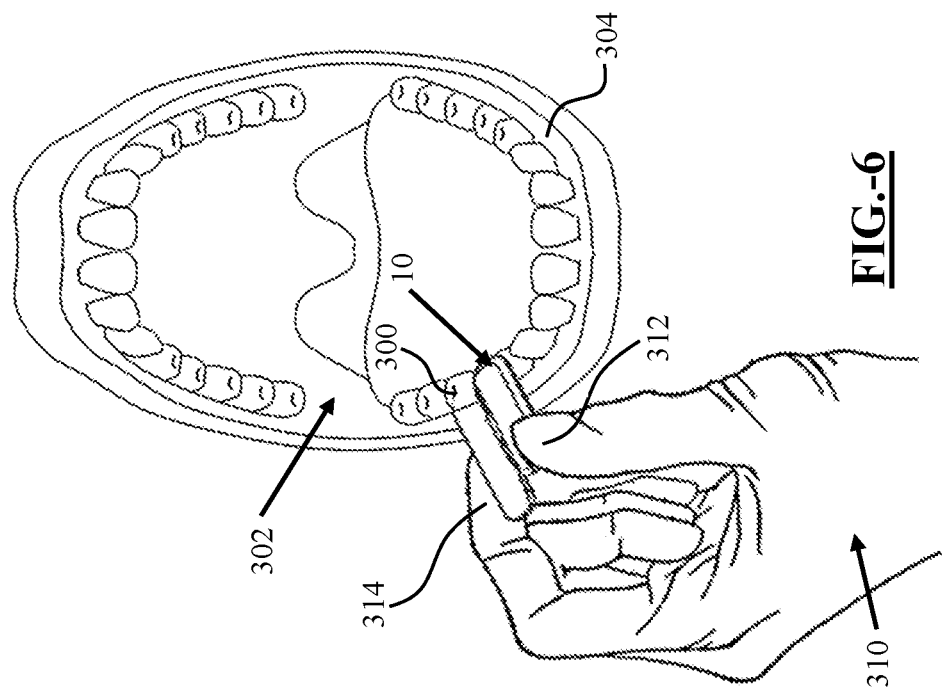
FIG. 6 illustrates a perspective view of an operator using a device according to the teachings to remove a dental covering from a mouth of a patient.

FIGS. 6 and 7 illustrate an operator using the device 10 to remove a dental covering 300. The operator holds the device 10 with his or her hand 310. The device 10 is located in a mouth 302 of a patient. The device 10 is located such that the load applying portion 14 rests on an adjacent surface 306. The device 10 is located such that the engagement portion 12 contacts a portion of the dental covering 300, such as between the gumline 304 and the dental covering 300. The operator applies the linear force $F_1$ to the load applying portion 14 with a first finger 312. The operator applies the rotational force (torque) $F_2$ with a second finger 314. The linear force $F_1$ and the rotational force $F_2$ combined are the prying load. The prying load results in the dental covering 300 being pried and lifted away from the gumline 304. Application of the prying load results in removal of the dental covering 300 with the device 10.

Figure 8:
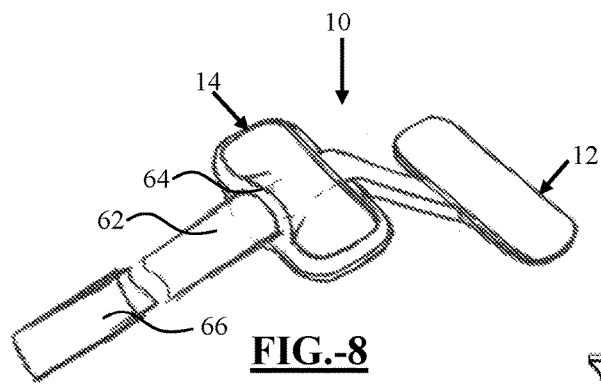
FIG. 8 illustrates a perspective view of a device with a handle according to the teachings.

FIG. 8 illustrates a perspective view of the device 10 which includes a handle 62. The handle 62 extends from the load applying portion 14. The load applying portion 14 includes a receptacle 64. The handle 62 is inserted and engaged with the receptacle 64. A connection end (not shown) of the handle 62 may have mating features to engage with the receptacle 64. The handle 62 includes a handle grip 66.

Figure 9:
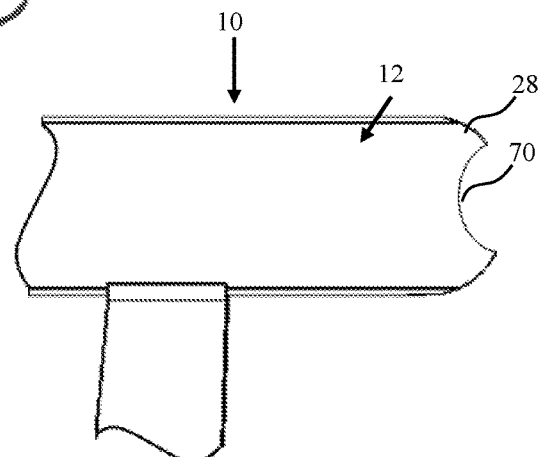
FIG. 9 illustrates a cutout in the device according to the teachings.

FIG. 9 illustrates a cut-out 70 in the device 10. The engagement portion 12 may include a cut-out 70 at the lateral end 28. It may be appreciated, the cut-out 70 may be located at a lateral end, front end, rear end, or any combination thereof of the engagement portion 12, the load applying portion 14, the intermediate portion 16, or any combination thereof. The cut-out 70 may help engage the engagement portion 12 with the dental covering 300 (not shown).

Figure 10:
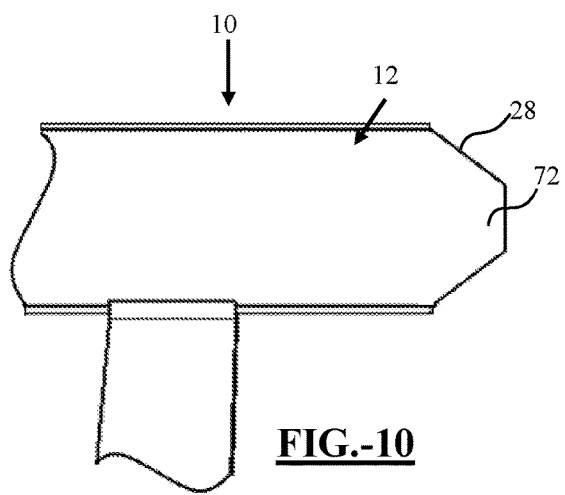
FIG. 10 illustrates an extension of the device according to the teachings.

FIG. 10 illustrates an extension 72 in the device 10. The engagement portion 12 may include an extension 72 at the lateral end 28. It may be appreciated, the extension 72 may be located at a lateral end, front end, rear end, or any combination thereof of the engagement portion 12, the load applying portion 14, the intermediate portion 16, or any combination thereof. The extension 72 may help engage the engagement portion 12 with the dental covering 300 (not shown).

Figure 11:
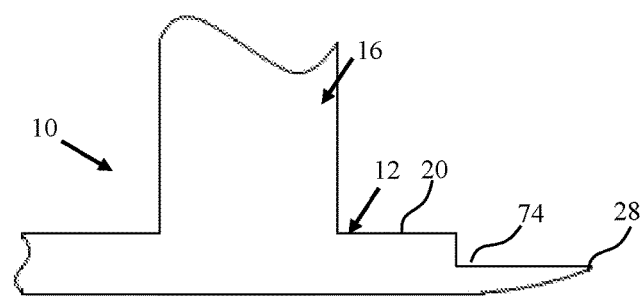
FIG. 11 illustrates a notch in the device according to the teachings.

FIG. 11 illustrates a notch 74 in the device 10. The engagement portion 12 may include a notch 74 in the upper surface 20 near the lateral end 28. It may be appreciated, the notch 70 may be located at a lateral end, front end, rear end, upper surface, lower surface or any combination thereof of the engagement portion 12, the load applying portion 14, the intermediate portion 16, or any combination thereof. The notch 74 may help engage the engagement portion 12 with the dental covering 300 (not shown).

FIGS. 12 and 13 illustrate a device 110 applied to a hemostat 160. The device 110 includes an engagement portion 112 and a load applying portion 114. The hemostat 160 may function as an intermediate portion 116 to connect the engagement portion 112 with the load applying portion 114. The hemostat 160 provides a handle grip 129 for a user to hold on to and control the device 110. The engagement portion 112 includes a first receptacle 126 (as shown in FIG. 14). The first receptacle 126 receives a tip 130 of the hemostat 160. The tip 130 cooperates with another tip 130 via a pivot joint 131 of the hemostat 160. The other tip 130 is received within a second receptacle 127 (as shown in FIG. 13). The second receptacle 127 is part of the load applying portion 114. The load applying portion 114 is off-set from the engagement portion 112 by being closer to the pivot joint 131 than the engagement portion 112.

FIGS. 14A and 14B illustrate the device 110 with a hemostat 160 removing a dental covering 300 from a patient's mouth 302. The load applying portion 114 rests on an adjacent surface 306 to the dental covering 300. The engagement portion 112 contacts a portion of the dental covering 300. The engagement portion 112 contacts a portion of the dental covering adjacent the gumline 304. The pivot joint 131 allows a distance between the engagement portion 112 and the load applying portion 114 to be adjusted. By adjusting the distance between the engagement portion 112 and the load applying portion 114, different heights of dental coverings 300 may be accommodated by the device 110.

Figure 15:
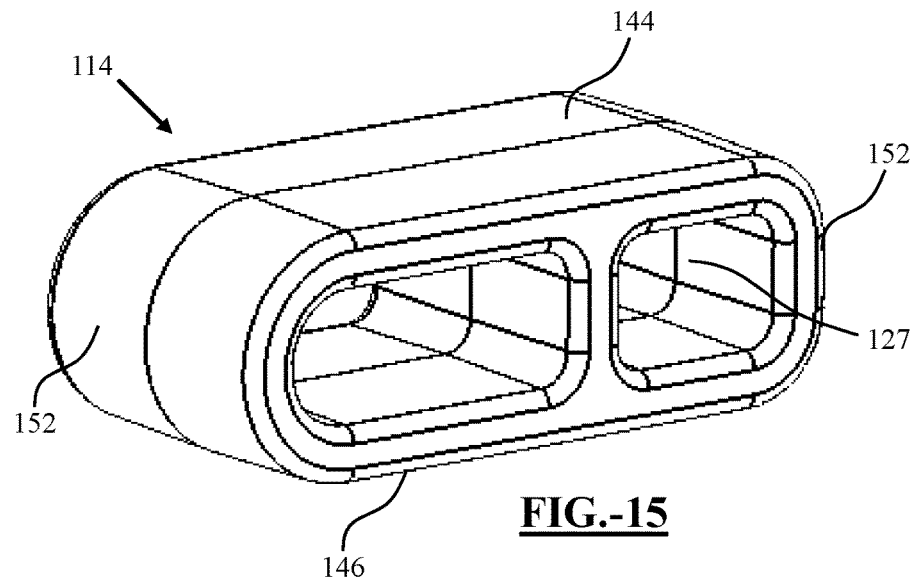
FIG. 15 illustrates a load applying portion having a receptacle according to the teachings.

FIG. 15 shows a load applying portion 114 of the device 110. The load applying portion 114 includes an upper surface 144 and a lower surface 146. The load applying portion 114 includes lateral ends 152 between the upper surface 144 and the lower surface 146. The load applying portion includes a second receptacle 127. The second receptacle 127 is located between the upper surface 144 and lower surface 146. The second receptacle 127 is located between the lateral ends 152. The second receptacle 127 receives a tip 130 (not shown) of the hemostat 160 (not shown).

Figure 16:
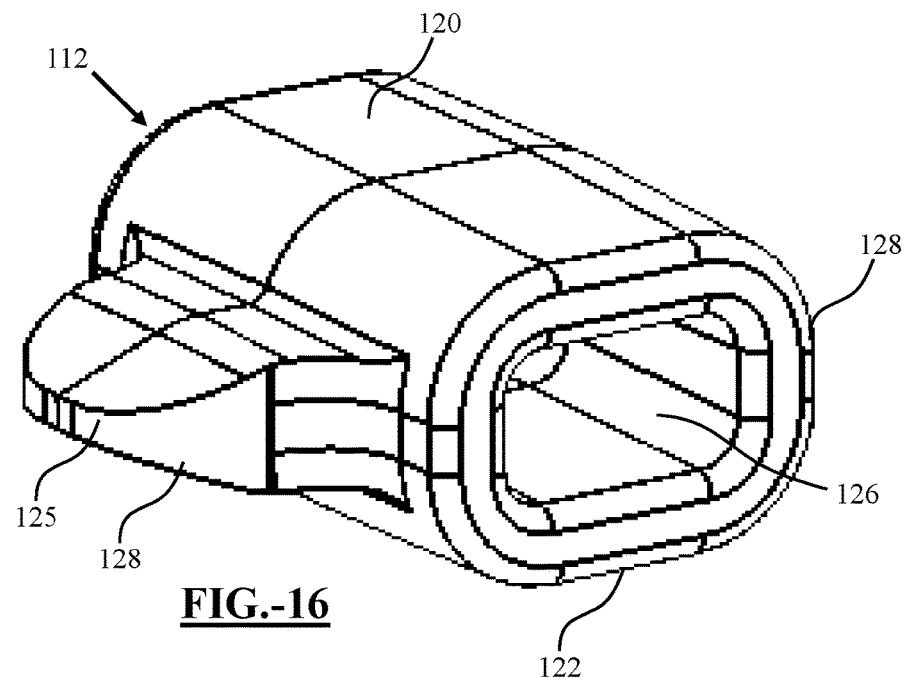
FIG. 16 illustrates an engagement portion having a receptacle according to the teachings.

FIG. 16 shows an engagement portion 112 of the device 110. The engagement portion 112 includes an upper surface 120 and a lower surface 122. The engagement portion 112 includes lateral ends 128 between the upper surface 120 and the lower surface 122. The engagement portion 112 includes a first receptacle 126. The first receptacle 126 is located between the upper surface 120 and the lower surface 122. The first receptacle 126 is located between the lateral ends 128. The first receptacle 126 receives a tip 130 (not shown) of the hemostat (160). The engagement portion 112 includes an off-set extension 125. The off-set extension 125 is located toward a lateral end 128. The off-set extension 125 is tapered towards a lateral end 128. The off-set extension 125 is substantially wedge-shaped to aid the engagement portion 112 engaging with a dental covering 300 (not shown).

Figure 17:
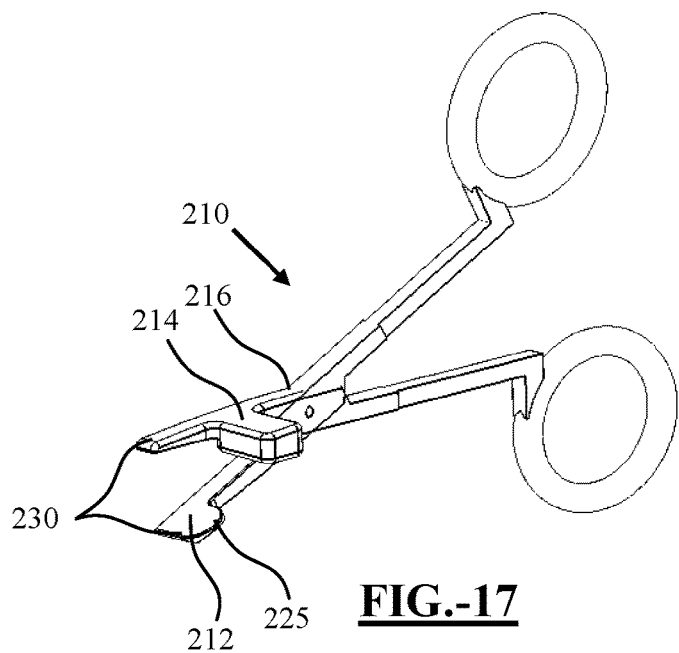
FIG. 17 illustrates a perspective view of the device integrated with a hemostat according to the teachings.
Figure 18:
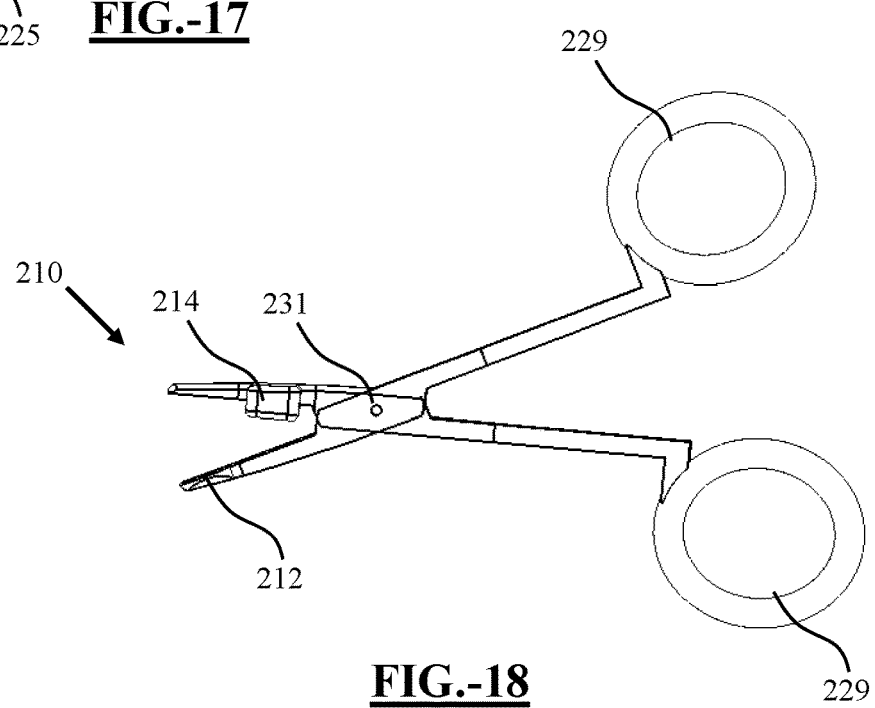
FIG. 18 illustrates a side view of the device integrated with a hemostat according to the teachings.

FIGS. 17 and 18 illustrate a device 210. The device 210 includes an engagement portion 212 connected to a load applying portion 214 via a pivot joint 231. The device 210 includes integrated handle grips 229 which rotate about the pivot joint 231. The handle grips 229 in combination with the pivot joint 231 may function as an intermediate portion 216 which connects the load applying portion 214 to the engagement portion 212. The device 210 includes a two tips 230. One of the tips 230 is integrated with the engagement portion 212. The engagement portion 212 includes an off-set extension 225. The off-set extension includes a tapered thickness. The off-set extension is configured to contact a portion of the dental covering 300 (not shown). One of the tips 230 is integrated with the load applying portion 214. The load applying portion 214 opposes the engagement portion 212.

REFERENCE NUMERAL LISTING

10—Device
12—Engagement portion

14—Load Applying portion
16—Intermediate portion
20—Upper surface of engagement portion
22—Lower surface of engagement portion
24—Front end of engagement portion
26—Rear end of engagement portion
28—Lateral ends of engagement portion
30—Beveled edges of engagement portion
32—Rounded corners of engagement portion
34—Upper surface of intermediate portion
36—Lower surface of intermediate portion
38—Front end of intermediate portion
40—Rear end of intermediate portion
42—Lateral ends of intermediate portion
44—Upper surface of load applying portion
46—Lower surface of load applying portion
48—Rear end of load applying portion
50—Front end of load applying portion
52—Lateral ends of load applying portion
54—Beveled edges of load applying portion
56—Rounded corners of load applying portion
58—Reinforcement structures
60—Ribs
62—Handle
64—Receptacle
66—Handle Grip
68—Fulcrum Point
70—Cut-out
72—Extension
74—Notch
110—Device
112—Engagement portion
114—Load Applying portion
116—Intermediate portion
120—Upper surface of engagement portion
122—Lower surface of engagement portion
125—Off-set extension of engagement portion
126—First receptacle of engagement portion
127—Second receptacle of load applying portion
128—Lateral ends of engagement portion
129—Handle grip
130—Tips of hemostat
131—Pivot joint
144—Upper surface of load applying portion
146—Lower surface of load applying portion
152—Lateral ends of load applying portion
160—Hemostat
210—Device
212—Engagement portion
214—Load Applying portion
216—Intermediate portion
225—Off-set extension
229—Handle grips
230—Tips of device
231—Pivot joint
300—Dental covering
302—Mouth of a patient
304—Gumline
306—Adjacent surface
310—Hand
312—First finger
314—Second finger
$F_1$—Prying Load (linear) at load applying portion
$F_2$—Prying load (rotational force) at engagement portion
$A_L$—Longitudinal Axis
$P_L$—Longitudinal plane
$P_T$—Transverse Plane
$P_T$—Single plane of intermediate portion
M—Midpoint
$\Theta_1$—Alternate exterior angle
$\Theta_2$—Alternate exterior angle
W—Width of Device
$W_E$—Width of Engagement Portion
$W_L$—Width of Load Prying Portion
$W_I$—Width of Intermediate Portion
L—Length of Device
$L_E$—Length of Engagement Portion
$L_L$—Length of Load Prying Portion
$L_I$—Length of Intermediate Portion
$T_E$—Thickness of Engagement Portion
$T_L$—Thickness of Load Prying Portion
$T_I$—Thickness of Intermediate Portion
H—Overall height of device Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. A device for removing a dental covering within a mouth of a patient comprising:
   (a) an engagement portion having a first plate portion, wherein the engagement portion is configured to contact a portion of the dental covering along only one of a facial side or a lingual side of the dental covering, and wherein the engagement portion is configured to receive at least one rotational force which is part of a prying load applied by an operator to rotate about a fulcrum;
   (b) a load applying portion connected to the engagement portion having a second plate portion, wherein the load applying portion includes a first surface adapted to rest upon an adjacent tooth relative to the dental covering and within the mouth, and a second surface opposing the first surface adapted to receive a linear force part of the prying load applied by the operator so that the load applying portion is the fulcrum;
   (c) an intermediate portion which is integral with and adjacent to both the engagement portion and the load applying portion which is configured to bridge the engagement portion and the load applying portion and resides generally in a single plane;
   (d) a longitudinal axis which generally extends from the engagement portion to the load applying portion and the device is sufficiently mirrored about the longitudinal axis to allow for ambidextrous use of the device;
      wherein the single plane of the intermediate portion is transverse to the first plate portion and the second plate portion, the first plate portion and the second plate portion each project away from the single plane so that the first plate portion forms a first angle with the intermediate portion and the second plate portion forms a second angle with the intermediate portion, and the first angle and the second angle are alternate exterior angles formed on opposite sides of the intermediate portion which are perpendicular or obtuse;
      wherein the intermediate portion is configured to avoid contact with any teeth or tissue adjoining the dental covering by having a width measured as a distance between two lateral ends and the width is smaller than a width of the load applying portion and smaller than a width of the engagement portion, wherein the width of the load applying portion is measured as a distance between lateral ends of the load applying portion which are opposing and the width of the engagement portion is measured as a distance between lateral ends of the engagement portion which are opposing; and
      wherein at least one of the lateral ends of the engagement portion is parallel to the longitudinal axis and at a least a portion of the engagement portion tapers to a smaller thickness toward the at least one of the lateral ends and away from the longitudinal axis so that the at least one of the lateral ends is adapted to be wedged between the dental covering and a gum line of the patient.

2. The device of claim 1, wherein the dental covering is for a mammal tooth; and
   wherein the dental covering includes a temporary crown, a permanent crown, a dental bridge, a dental brace, a dental veneer, an artificial tooth, or any combination thereof.

3. The device of claim 2, wherein the portion of the dental covering is an extremity of the dental covering.

4. The device of claim 1, wherein the device is a unitary structure.

5. The device of claim 1, wherein the engagement portion, the load applying portion, and the intermediate portion are a unitary structure; and
   wherein the device includes a handle having one or more receptacles which have the load applying portion, the engagement portion, or both located therein.

6. The device of claim 5, wherein the one or more receptacles have a geometry reciprocal with a geometry of the load applying portion, the engagement portion, or both; and
   wherein the load applying portion, the engagement portion, or both are retained within the one or more receptacles via a friction fit.

7. The device of claim 1, wherein the device includes a handle extending from the load applying portion.

8. The device of claim 1, wherein the second plate portion, a receptacle of the load applying portion, or both are adapted to receive and engage a handle.

9. The device of claim 1, wherein the intermediate portion includes a midpoint between the engagement portion and the load applying portion;
   wherein a transverse plane parallel to the longitudinal axis intersects the midpoint; and
   wherein the engagement portion is on an opposing side of the transverse plane relative to the load applying portion such that the engagement portion resides entirely on the opposing side of the transverse plane relative to the load applying portion, and both the engagement portion and the load applying portion do not intersect the transverse plane.

10. The device of claim 1, wherein the device includes one or more reinforcement structures extending from the intermediate portion into at least part of the engagement portion, the load applying portion, or both so that the device is sufficiently rigid to withstand the prying load and transmit at least a portion of the prying load to the engagement portion.

11. The device of claim 1, wherein the first plate portion and the second plate portion are flat; and
    wherein the first plate portion is generally parallel to and distanced from the second plate portion.

12. A method of using a device to remove a dental covering from a mouth of a patient comprising:
    (i) contacting an engagement portion of the device to a base of the dental covering and locating the engagement portion between the base of the dental covering and a gum line of the patient, wherein the engagement portion includes a first plate portion, wherein the engagement portion includes one or more lateral ends parallel to a longitudinal axis of the device, and wherein at least a portion of the engagement portion tapers to a smaller thickness toward the one or more lateral ends and away from the longitudinal axis so that the one or more lateral ends are wedged between the dental covering and the gum line of the patient;

(ii) resting a load applying portion of the device upon an adjacent tooth relative to the dental covering, wherein the load applying portion includes a second plate portion distanced from the first plate portion, wherein the load applying portion includes a first surface which rests upon the adjacent tooth and a second surface opposite the first surface, and wherein the load applying portion is connected to the engagement portion via an intermediate portion which is integral with and adjacent to both the engagement portion and the load applying portion and which is configured to bridge the engagement portion and the load applying portion and resides generally in a single plane; and (iii) applying a prying load by a hand of an operator to the device and removing the dental covering from the mouth of the patient, wherein applying the prying load includes applying a linear force to the load applying portion such that the load applying portion remains in contact with the adjacent tooth and is a fulcrum and applying a torque to the engagement portion so that the engagement portion rotates about the fulcrum;

wherein the longitudinal axis generally extends from the engagement portion to the load applying portion and the device is sufficiently mirrored about the longitudinal axis to allow for ambidextrous use of the device;

wherein the single plane of the intermediate portion is transverse to the first plate portion and the second plate portion, the first plate portion and the second plate portion each project away from the single plane so that the first plate portion forms a first angle with the intermediate portion and the second plate portion forms a second angle with the intermediate portion, and the first angle and the second angle are alternate exterior angles formed on opposite sides of the intermediate portion which are perpendicular or obtuse; and wherein the intermediate portion is configured to avoid contact with any teeth or tissue adjoining the dental covering by having a width measured as a distance between two lateral ends and the width is smaller than a width of the load applying portion and smaller than a width of the engagement portion, wherein the width of the load applying portion is measured as a distance between lateral ends of the load applying portion which are opposing and the width of the engagement portion is measured as a distance between lateral ends of the engagement portion which are opposing.

13. The method of claim 12, wherein a first finger of the operator applies the linear force and a second finger of the operator applies the torque.

14. The method of claim 12, wherein the method includes engaging a handle with the load applying portion.

15. The method of claim 14, wherein the method includes inserting the handle into the load applying portion or inserting the load applying portion into the handle.

16. The method of claim 12, wherein the locating the engagement portion between the base of the dental covering and the gum line includes wedging one of the one or more of the lateral ends between the dental covering and the gum line of the patient.

17. The method of claim 12, wherein the first plate portion and the second plate portion are flat; and wherein the first plate portion is generally parallel to and distanced from the second plate portion.

18. The method of claim 12, wherein the dental covering is for a mammal tooth; and wherein the dental covering includes a temporary crown, a permanent crown, a dental bridge, a dental brace, a dental veneer, an artificial tooth, or any combination thereof.

* * * * *